(12) United States Patent
Joshi

(10) Patent No.: US 11,200,042 B1
(45) Date of Patent: Dec. 14, 2021

(54) DYNAMIC CONTROL OF EVENT DEPENDENT USER FEEDBACK

(71) Applicant: ALLSCRIPTS SOFTWARE, LLC, Chicago, IL (US)

(72) Inventor: Nikhil Rajeev Joshi, Pune (IN)

(73) Assignee: Allscripts Software, LLC, Chicago, IL (US)

( * ) Notice: Subject to any disclaimer, the term of this patent is extended or adjusted under 35 U.S.C. 154(b) by 672 days.

(21) Appl. No.: 15/157,484

(22) Filed: May 18, 2016

(51) Int. Cl.
*G06F 9/44* (2018.01)
*G06F 8/65* (2018.01)
*G16H 10/60* (2018.01)

(52) U.S. Cl.
CPC .............. *G06F 8/65* (2013.01); *G16H 10/60* (2018.01)

(58) Field of Classification Search
CPC ........................................................ G06F 9/44
USPC ................................................. 717/168–178
See application file for complete search history.

(56) References Cited

U.S. PATENT DOCUMENTS

| 2003/0050797 | A1* | 3/2003 | Brandt | G06Q 10/10 705/2 |
| 2007/0067184 | A1* | 3/2007 | Harp | G16H 40/67 705/2 |
| 2013/0036210 | A1* | 2/2013 | Birtwhistle | G16H 40/40 709/221 |
| 2015/0017964 | A1* | 1/2015 | Cha | H04W 4/60 455/418 |
| 2016/0335710 | A1* | 11/2016 | Piper | H04W 68/04 |

* cited by examiner

*Primary Examiner* — Jae U Jeon
(74) *Attorney, Agent, or Firm* — Loza & Loza, LLP; Peter Zura

(57) ABSTRACT

A method includes providing, by a healthcare software provider, an updated version of a healthcare software application; maintaining a list of events each mapped to one or more actions to be taken upon occurrence of such event; generating, by an instance of the updated version of the healthcare software application running on an electronic device, a log of events representing user actions; looking up in the maintained list of events, based on the occurrence of a logged event, a mapped action to take in response thereto, the mapped action being to provide a first user notification; and providing, in the healthcare software application, the first user notification.

20 Claims, 4 Drawing Sheets

DYNAMIC CONTROL OF EVENT DEPENDENT USER FEEDBACK

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to software notification methodologies.

Frequently, when a product is released or updated, release notes are provided documenting features and functionality related to the software. Typically, release notes might be provided in a text file or a pdf document, or accessible online. However, a user can find the amount of information contained in these release notes overwhelming, and may not read or digest all of the information contained therein.

In the context of healthcare software, a software provider may wish to on occasion provide safety notifications regarding software. For example, such safety notifications may be in the form of an email. However, these safety notifications may be ignored or forgotten about when it comes time to actually utilize the software such safety notifications are applicable to.

A need exists for improvement in software notification methodologies. This need and other needs are addressed by one or more aspects of the present invention.

SUMMARY OF THE INVENTION

The present invention includes many aspects and features. Moreover, while many aspects and features relate to, and are described in, the context of healthcare software, the present invention is not limited to use only in this context, as will become apparent from the following summaries and detailed descriptions of aspects, features, and one or more embodiments of the present invention.

Accordingly, one aspect of the present invention relates to a method comprising providing, by a healthcare software provider, an updated version of a healthcare software application; maintaining a list of events each mapped to one or more actions to be taken upon occurrence of such event; generating, by an instance of the updated version of the healthcare software application running on an electronic device, a log of events representing user actions; looking up in the maintained list of events, based on the occurrence of a logged event, a mapped action to take in response thereto, the mapped action being to provide a first user notification; and providing, in the healthcare software application, the first user notification.

In a feature of this aspect, the healthcare software application comprises an electronic health records software application.

In a feature of this aspect, the electronic device comprises a desktop computer.

In a feature of this aspect, the electronic device comprises a server.

In a feature of this aspect, the electronic device comprises a laptop.

In a feature of this aspect, the electronic device comprises a tablet.

In a feature of this aspect, the electronic device comprises a phone.

Another aspect relates to a method comprising providing, by a healthcare software provider, an updated version of a healthcare software application; maintaining a list of events each mapped to one or more actions to be taken upon occurrence of such event; generating, by an instance of the updated version of the healthcare software application running on an electronic device, a log of events representing user actions; looking up in the maintained list of events, based on the occurrence of a logged event, a mapped action to take in response thereto, the mapped action being to provide a first safety notification; and providing, in the healthcare software application, the first safety notification.

Another aspect relates to a method comprising maintaining a list of events for a healthcare software application each mapped to one or more actions to be taken upon occurrence of such event, the list of events including a first event mapped to a first action comprising provision of a first user notification; generating, by an instance of the healthcare software application running on an electronic device, a first log of events representing user actions; looking up in the maintained list of events, based on the occurrence of the first event, the first action to take in response thereto, the first action comprising provision of a first user notification; providing, in the healthcare software application, the first user notification; updating the maintained list of events to map the first event to a second action comprising provision of a second user notification; generating, by an instance of the healthcare software application running on an electronic device, a second log of events representing user actions; looking up in the maintained list of events, based on the occurrence of the first event, the second action to take in response thereto, the second action comprising provision of a second user notification; and providing, in the healthcare software application, the second user notification.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein, FIG. 1 illustrates an exemplary interface of a first version of an electronic health records software application that allows a user to input temperature vital information;

FIG. 4 illustrates exemplary user feedback regarding a safety issue.

DETAILED DESCRIPTION

Figure 2:
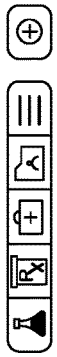
FIG. 2 illustrates an exemplary updated interface of an updated second version the electronic health records software application of FIG. 1.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

As noted above, although release notes are often provided documenting features and functionality related to software when it is released or updated, users may not always read or remember information contained in such release notes.

In accordance with one or more preferred implementations, distributed software or a computer system is configured to generate unique events or to include unique identifiers for identifying its own state or the state of another software.

In accordance with one or more preferred implementations, this serves to allow for publishing of a list of actions mapped with those events or identifiers, so that the publisher of such mapping can dynamically control behavior of the distributed software or computer system, as and when it reaches the state associated with the event or identifier. Thus, the publisher can dynamically change behavior of software without changing the software code, and the behavior is changed merely by modifying the published list or mapping.

In accordance with one or more preferred implementation, software includes the ability to write a log of user actions (which may be characterized as events) as and when a user accesses various features of the software. The software includes an ability to monitor the log, so that the software can reconcile the areas accessed by the user with the list of published actions mapped to those areas. Preferably, the software can trigger a user feedback action as and when a log entry is created to denote that the user has accessed certain feature of the software.

Figure 1:
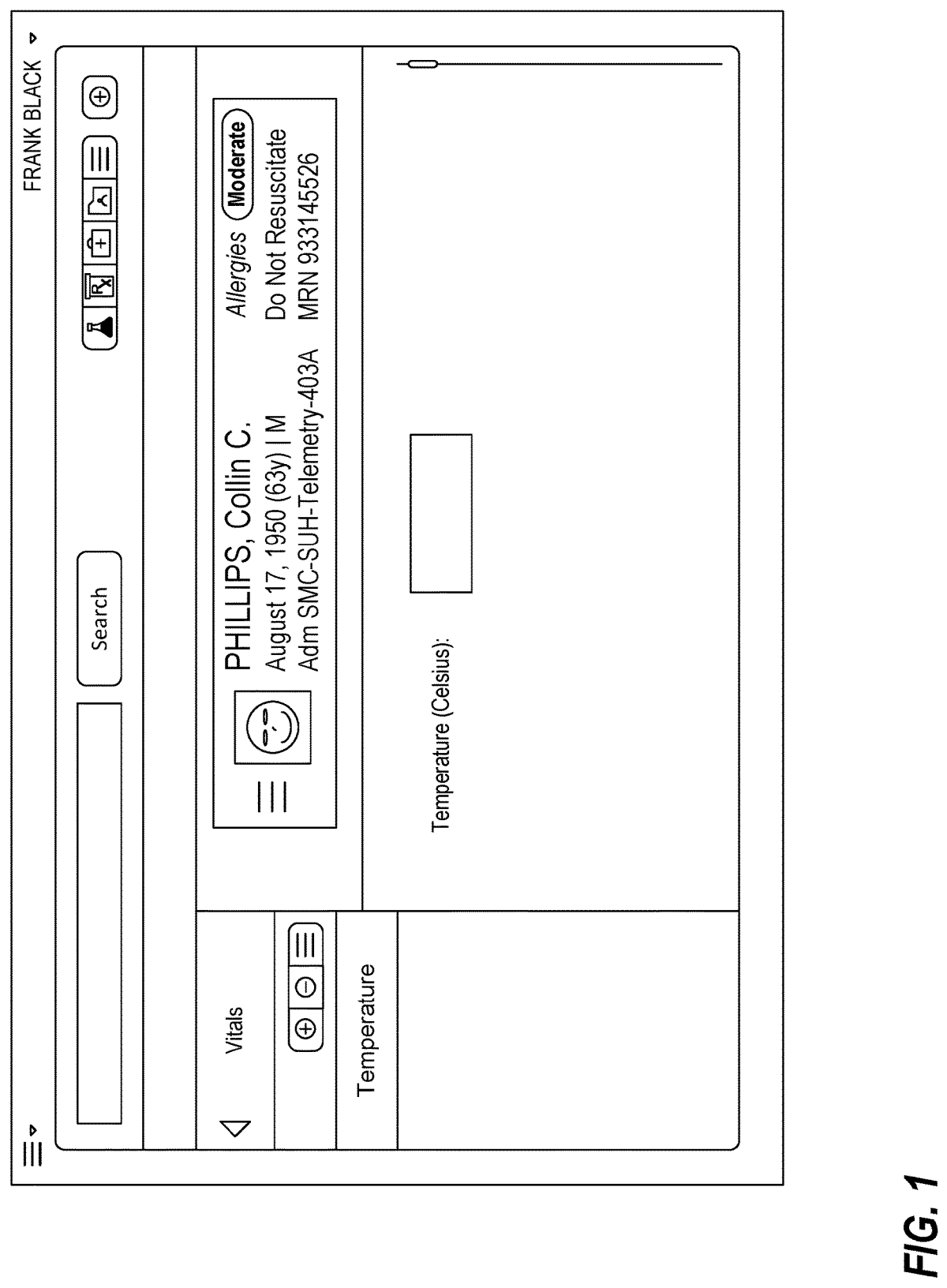
Figure 3:
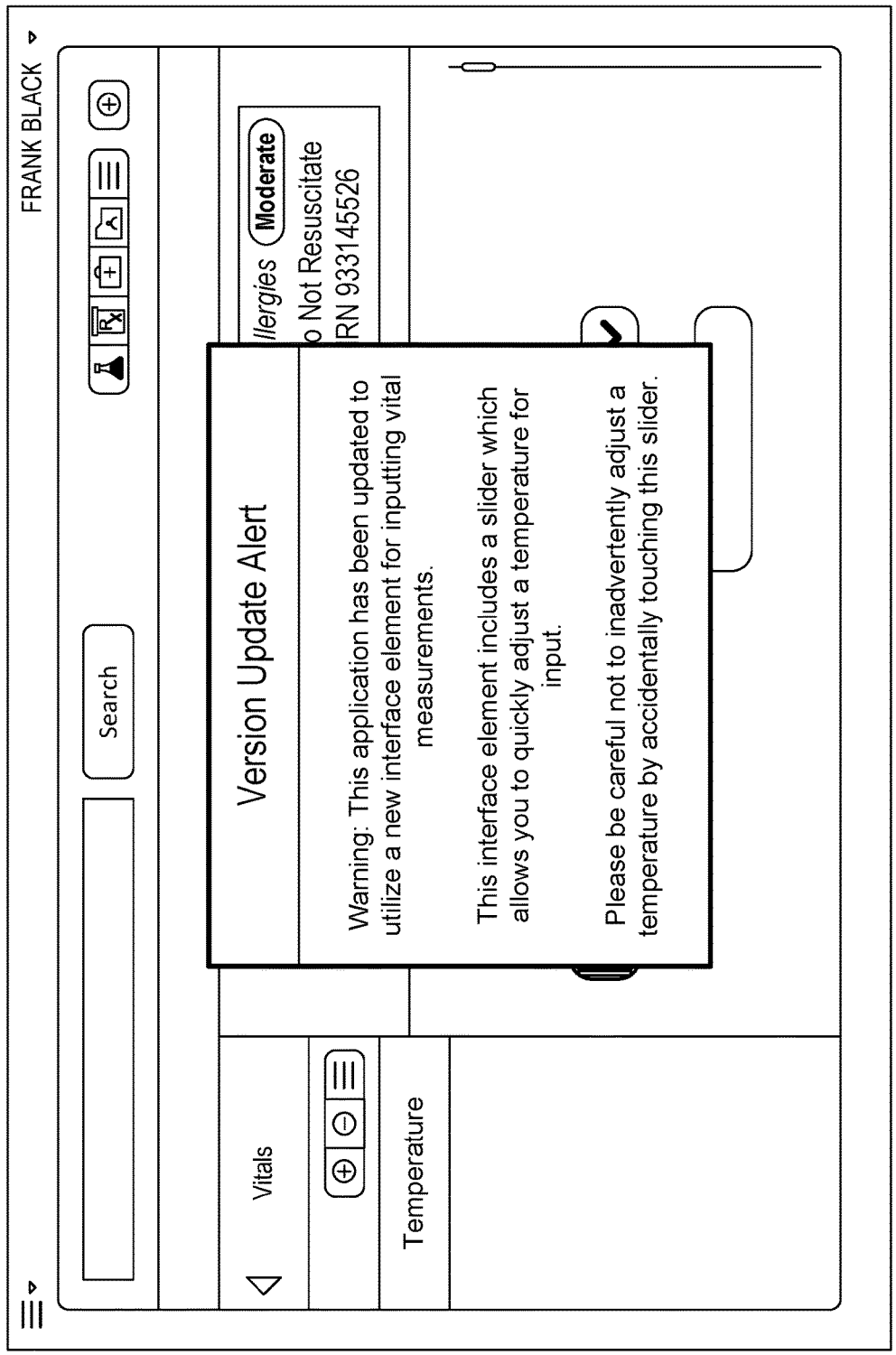
FIG. 3 illustrates the display of user feedback in the form of release notes regarding a new user interface element.

In accordance with one or more preferred implementations, triggered user feedback is a context sensitive portion of release notes about some new feature of that area of the software that has been updated in that version. For example, FIG. 1 illustrates an exemplary interface of a first version of an electronic health records software application that allows a user to input temperature vital information. In an updated second version of the electronic health records software application, a new user interface element is utilized to facilitate input of temperature vital information, as illustrated in FIG. 2. In accordance with one or more preferred implementations, when a user accesses this portion of the application (e.g. for the first time), user feedback is triggered which displays release notes regarding such new user interface elements, as illustrated in FIG. 3.

Figure 4:
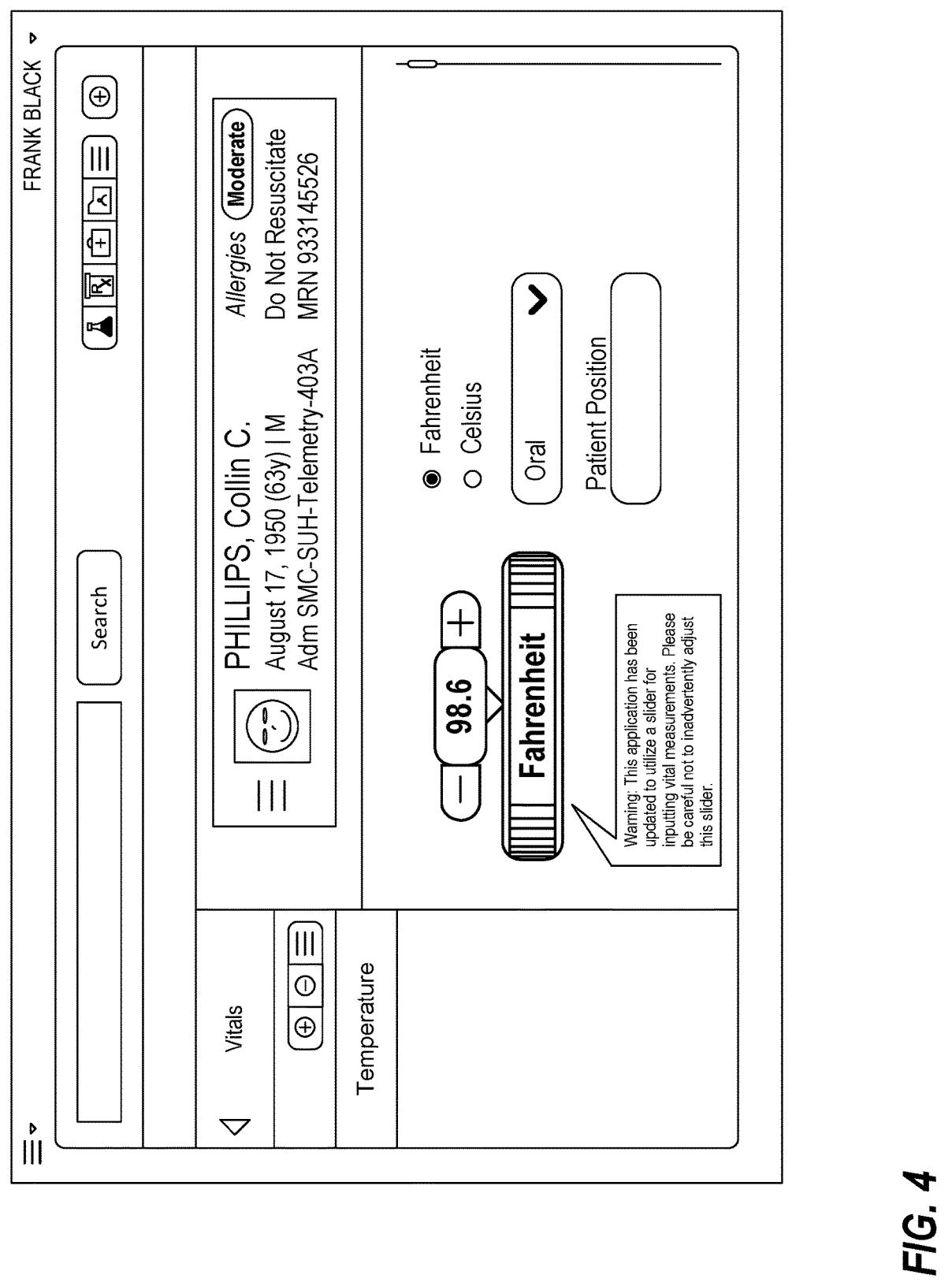

In accordance with one or more preferred implementations, triggered user feedback is a patient safety notification alert to indicate that a bug or a potential safety issue has been identified in that area of the software, including instructions for mitigating effects of the bug or issue. FIG. 4 illustrates such exemplary user feedback.

In accordance with one or more preferred implementations, triggered user feedback can be a combination of an audible alert, a flashing area of a software user interface, or a pop-up window containing a context specific message for which a mapping with that area of software has been published.

In accordance with one or more preferred implementations, software includes a global variable, and code behind various areas of the software assigns unique values to the global variable as and when that part of the code is executed. The software includes an ability to monitor the value of the global variable, so that the software can trigger user feedback as and when the variable gets assigned a unique value that has been mapped to a specific user feedback. This will be meaningful because the variable's assignment to that unique value denotes that the user has accessed certain feature of the software for which the publisher has mapped a specific user feedback.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method comprising:
   (a) activating an updated version of a healthcare software application that differs from a previous version of the healthcare software application;
   (b) maintaining a list of events each mapped to one or more actions to be taken upon occurrence of each event, wherein the list of events comprises log entries of accessed features associated with the operation of the previous version of the healthcare software application;
   (c) generating, by an instance of the updated version of the healthcare software application running on an electronic device, a log of updated events representing user actions for the updated version of the healthcare software application comprising log entries of accessed features associated with the operation of the updated healthcare software application;
   (d) determining, from the maintained list of events, based on an occurrence of a first logged updated event, a mapped action to take relative to respective accessed features associated with the operation of the updated healthcare software application in response thereto, the mapped action being to provide a first user notification; and
   (e) providing, in the updated version of the healthcare software application, the first user notification.

2. The method of claim 1, wherein the healthcare software application comprises an electronic health records software application.

3. The method of claim 1, wherein the electronic device comprises a desktop computer.

4. The method of claim 1, wherein the electronic device comprises a server.

5. The method of claim 1, wherein the electronic device comprises a laptop.

6. The method of claim 1, wherein the electronic device comprises a tablet.

7. The method of claim 1, wherein the electronic device comprises a phone.

8. A method comprising:
   (a) activating an updated version of a healthcare software application that differs from a previous version of the healthcare software application;
   (b) maintaining a list of events each mapped to one or more actions to be taken upon occurrence of each event, wherein the list of events comprises log entries of accessed features associated with the operation of the previous version of the healthcare software application;
   (c) generating, by an instance of the updated version of the healthcare software application running on an electronic device, a log of updated events representing user actions for the updated version of the healthcare software application comprising log entries of accessed features associated with the operation of the updated healthcare software application;
   (d) determining, from the maintained list of events, based on the occurrence of a first logged updated event, a mapped action to take relative to respective accessed features associated with the operation of the updated healthcare software application in response thereto, the mapped action being to provide a first safety notification; and
   (e) providing, in the healthcare software application, the first safety notification.

9. The method of claim 8, wherein the healthcare software application comprises an electronic health records software application.

10. The method of claim 8, wherein the electronic device comprises a desktop computer.

11. The method of claim 8, wherein the electronic device comprises a server.

12. The method of claim 8, wherein the electronic device comprises a laptop.

13. The method of claim 8, wherein the electronic device comprises a tablet.

14. The method of claim 8, wherein the electronic device comprises a phone.

15. A method comprising:
   (a) maintaining a list of events for a healthcare software application each mapped to one or more actions to be taken upon occurrence of each event, wherein the list of events comprises log entries of accessed features associated with the operation of the previous version of the healthcare software application, and wherein the list of events includes a first event mapped to a first action comprising provision of a first user notification;
   (b) generating, by an instance of the healthcare software application running on an electronic device, a first log of events representing user actions, the first log of events comprising log entries of accessed features associated with the operation of the updated healthcare software application;

(c) determining from the maintained list of events, based on the occurrence of the first event, the first action to take in response thereto the first log of events comprising log entries of accessed features associated with the operation of the updated healthcare software application, the first action comprising provision of a first user notification;

(d) providing, in the healthcare software application, the first user notification;

(e) updating the maintained list of events to map the first event to a second action comprising provision of a second user notification;

(f) generating, by an instance of the healthcare software application running on an electronic device, a second log of events representing user actions, the second log of events comprising further log entries of accessed features associated with the operation of the updated healthcare software application;

(g) determining, from the maintained list of events, based on the occurrence of the first event, the second action to take in response thereto the second log of events comprising further log entries of accessed features associated with the operation of the updated healthcare software application, the second action comprising provision of a second user notification; and (h) providing, in the healthcare software application, the second user notification.

16. The method of claim 15, wherein the healthcare software application comprises an electronic health records software application.

17. The method of claim 15, wherein the electronic device comprises a desktop computer.

18. The method of claim 15, wherein the electronic device comprises a server.

19. The method of claim 15, wherein the electronic device comprises a laptop.

20. The method of claim 15, wherein the electronic device comprises a tablet.

* * * * *